United States Patent

Fujiwara et al.

Patent Number: 6,114,121
Date of Patent: Sep. 5, 2000

[54] NUCLEIC ACID PROBE MOLECULE OF HAIRPIN-SHAPE STRUCTURE AND METHOD FOR DETECTING NUCLEIC ACIDS USING THE SAME

[75] Inventors: Jun Fujiwara; Yasushi Shigemori, both of Tokyo, Japan

[73] Assignee: Aisin Cosmos R&D Co., Ltd., Aichi-Ken, Japan

[21] Appl. No.: 08/969,320

[22] Filed: Nov. 13, 1997

[30] Foreign Application Priority Data

Nov. 14, 1996 [JP] Japan .................................. 8-316906

[51] Int. Cl.[7] .............................. C12Q 1/68; C07H 21/02; C07H 21/04; C12N 15/00
[52] U.S. Cl. ............................ 435/6; 536/23.1; 536/24.3; 935/76; 935/77; 935/78
[58] Field of Search ................................ 435/6; 536/23.1, 536/24.3; 935/76, 77, 78

[56] References Cited

U.S. PATENT DOCUMENTS

| | | | |
|---|---|---|---|
| 4,888,274 | 12/1989 | Radding et al. ............................. | 435/6 |
| 5,215,899 | 6/1993 | Dattagupta .................................. | 435/6 |
| 5,506,098 | 4/1996 | Zarling et al. .............................. | 435/6 |
| 5,670,316 | 9/1997 | Sena et al. .................................. | 435/6 |
| 5,731,411 | 3/1998 | Voloshin et al. .......................... | 530/326 |
| 5,733,733 | 3/1998 | Auerbach .................................... | 435/6 |

OTHER PUBLICATIONS

Krupp et al., FEBS Letters 212(2) : 271–275 (1987).
Krupp, Gene 72 : 75–89 (1988).
Revet et al., J. of Molecular Biology 232 : 779–791 (1993).
Honigberg et al., PNAS 83 : 9586–9590 (1986).
Bryant et al., PNAS 82 : 297–301 (1985).
Kirkpatrick et al., Nucleic Acids Research 20(16) : 4339–4353 (1992).

*Primary Examiner*—W. Gary Jones
*Assistant Examiner*—Ethan Whisenant
*Attorney, Agent, or Firm*—John P. White; Cooper & Dunham LLP

[57] ABSTRACT

This invention provides a hairpin-shaped nucleic acid probe which is capable of forming stable hybrid with target nucleic acid, and a method for detecting nucleic acid containing a sequence complementary to a part of sequence of the probe. After contacting RecA to a hairpin-shaped single strand probe for hybridization, this complex is contacted with a target nucleic acid to form a triplex recombination intermediate using RecA function. After ligating the probe and the target nucleic acid, the target nucleic acid is detected by the label on the probe.

3 Claims, 2 Drawing Sheets

| LANE | RecA | LIGASE |
|------|------|--------|
| 1    | −    | −      |
| 2    | +    | −      |
| 3    | −    | +      |
| 4    | +    | +      |

| LANE | RecA | LIGASE |
|------|------|--------|
| 1    | −    | −      |
| 2    | +    | −      |
| 3    | −    | +      |
| 4    | +    | +      |

SEQUENCE LISTING

<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: Description of Artificial Sequence: synthetic
            DNA

<400> SEQUENCE: 1
gtcatgccat ccgtaagatg cttttctgtg actggtgagt gcggccgcgg tttccgcggc    60
cgc                                                                  63

NUCLEIC ACID PROBE MOLECULE OF HAIRPIN-SHAPE STRUCTURE AND METHOD FOR DETECTING NUCLEIC ACIDS USING THE SAME

BACKGROUND OF THE INVENTION

1. Field of the Invention

This invention relates to nucleic acid probe molecules of hairpin-shaped structure and methods for detecting nucleic acids using the probe.

2. Description of the Prior Art

A variety of nucleic acid detection methods has been applied to a diagnosis of diseases, judgement of a species of animals and plants, judgement of parents and children, DNA cloning and the like. The prior art of detecting nucleic acid includes a method employing labeled probes, such as Southern hybridization. A variety of improvements have been made in these methods.

An example of the improvements is a target DNA detection method, wherein by an enzymatic reaction using RecA proteins, a recombination intermediate is formed between a target DNA and an oligonucleotide used as a probe (Cheng et al., J. Biol. Chem. 263, 15110–15117, 1988). However, the intermediate is unstable, especially after deproteinization. Therefore, Cheng et al. formed a stable recombination intermediate using light bridging. However, the light bridging causes non-specific binding of the probe to a target DNA and a damage of the target DNA due to the ultraviolet irradiation during the light bridging.

Another improvement has been also known, wherein the defects inherent to the prior art described above can be partially solved. This improvement is use of a padlock-shaped oligonucleotide probe, wherein both ends of the probes are hybridized to the adjoining sequences in a target DNA, and then both ends of the probe are ligated to form a more stable hybrid (Nilsson et al., Science, 265, 2085, 1994). Yet, in this method, the target nucleic acid molecule must be single strand. Therefore one cannot perform analysis of a double strand DNA such as genomic DNA.

SUMMARY OF THE INVENTION

The above shown prior arts have defects and faults that the subsequent analysis is hampered by the damage to the target nucleic acid molecule, or only single strand is detected. The purpose of the present invention is to provide the following nucleic acid probe molecules for hybridization, as well as the following method for detecting nucleic acid using the nucleic acid probe molecules:

1) a method for detecting a target double-stranded nucleic acid;

2) a hairpin-shaped nucleic acid probe molecule which is capable of forming a stable hybrid with a target nucleic acid;

3) a method for detecting a nucleic acid having a sequence complementary to the sequence contained in the nucleic acid probe, wherein the hairpin-shaped nucleic acid molecule of 2) is hybridized to the target nucleic acid and the formed hybrid is detected.

To solve the technical problems in the prior art and achieve the purposes, the present invention provides the following nucleic acid probe molecules and method for detecting a target nucleic acid molecule.

(1) A nucleic acid probe molecule according to the present invention comprises the first nucleotide portion with self-complementary stem-and-loop structure, and the second nucleotide portion with single strand structure extending from one end of the first nucleotide portion, wherein the second nucleotide portion is complementary to the nucleic acid sequence for detection. Preferably, the second nucleotide portion is at least 15 bases of nucleotide and the first nucleated portion is at least 13 bases of nucleotide. Preferably, the nucleic acid probe is further labeled with a detectable marker.

(2) A method according to the present invention is for detecting a target nucleic acid molecule by means of hybridization of a target nucleic acid with a labeled nucleic probe, the target nucleic acid having a desired sequence which is complementary to the sequence contained in the probe: the method comprising the first step of forming a probe-RecA complex by binding RecA proteins to the nucleic acid probe; the second step of contacting the target nucleic acid with the complex, thereby forming a hybrid between the target nucleic acid molecule and a part or all of the probe; the third step of ligating the probe and the target nucleic acid molecule by reacting a ligase between the end of the target nucleic acid in the hybrid and the end of the first nucleotide portion in the probe; the fourth step of removing proteins from the hybrid; the fifth step of separating unhybridized probe from the hybrid followed by detecting the label of the nucleic acid probe contained in the hybrid.

Preferably, the target nucleic acid molecule is double stranded DNA and the ligase is NAD requiring type. Preferably, the reaction using the ligase is performed in the solution of 37 to 65° C.

DETAILED DESCRIPTION OF THE INVENTION

The present invention is illustrated by the following examples. However, it should be understood that the invention is not limited to the specific details of these examples. This is obvious to those skilled in the art.

Figure 1:
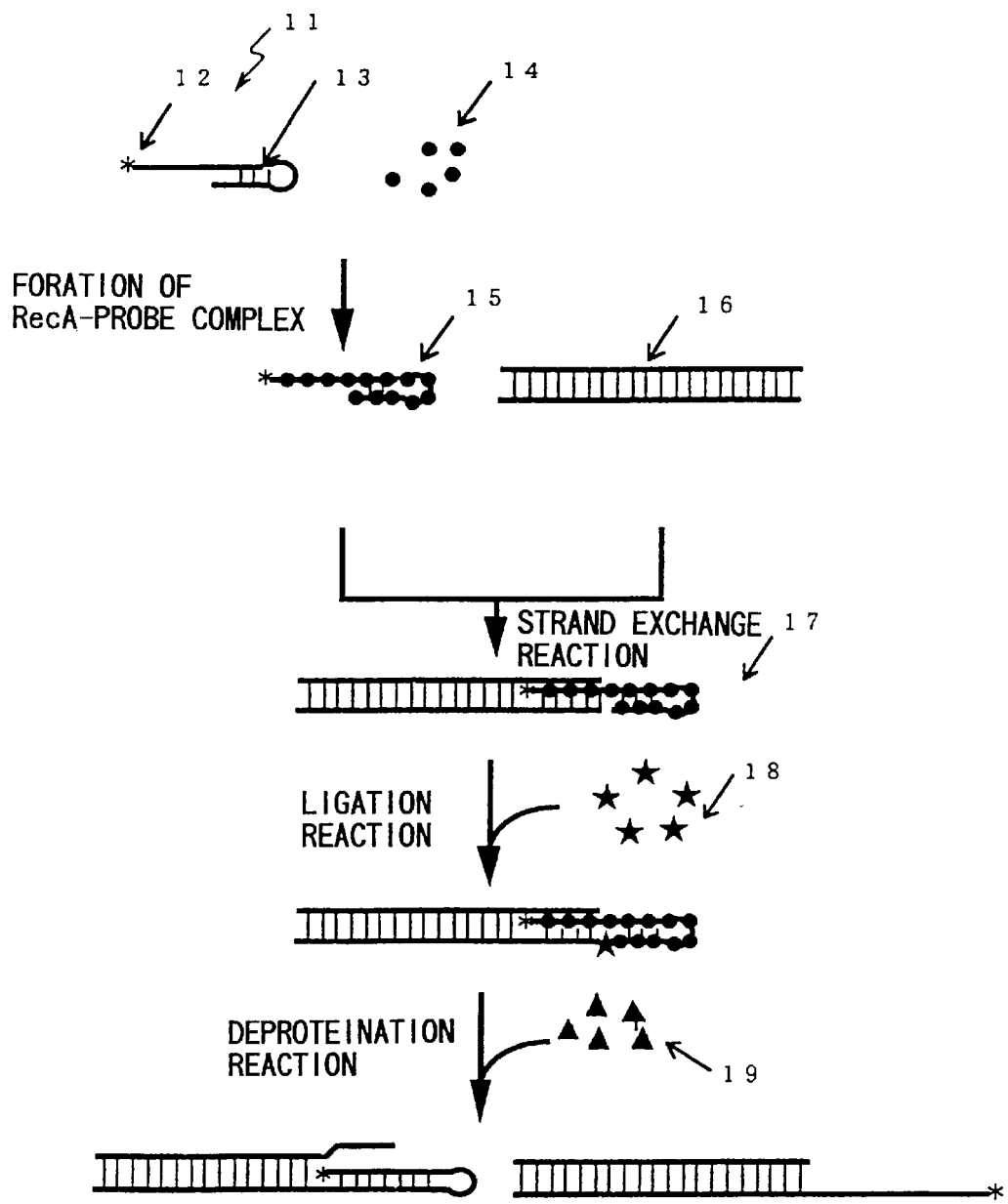
FIG. 1 shows an outline of the method for detecting nucleic acid employing the hairpin-shaped nucleic acid probe of the present invention.

FIG. 1 shows a method for detecting double stranded DNA utilizing a hairpin-shaped DNA probe of the present invention. The hairpin-shaped DNA probe molecule which best illustrates the present invention and the method for detecting a target double stranded DNA molecule utilizing said DNA probe molecule are explained with reference to the FIG. 1.

Hairpin shaped nucleic acid probe molecule

FIG. 1 shows a hairpin-shaped DNA probe molecule (11) for recognition and detection of the end sequence of the target DNA molecule (16). Said probe (11) is labeled with 32P at its 5' terminus by the method well known in the art. The 5' terminus of said probe (11) has a portion complementary to the terminal sequence of the target DNA (16) (between label (12) and the stem-and-loop structure (13)), and the 3' terminus of said probe has a sequence (13) of self-complementary stem-and-loop structure. The portion complementary to the terminal sequence in the target DNA (16) is long enough to form a stable intermediate with the probe during strand exchange reaction and the following ligation reaction. Preferably, the length is at least 15 nucleotides. However, said length of the probe (necessary for stabilizing the intermediate during the strand exchange reaction and the ligation reaction) is affected by the characteristics of the target DNA such as GC content, and the reaction condition such as temperature and the salt concentration of the reaction solution. This is obvious to the skilled in the art and it is also obvious that they adjust the length of the probe according to the characteristics of the terminal sequence of the target DNA and the reaction condition. Therefore, the portion complementary to the terminal sequence of the target DNA enables the probe itself to form a stable intermediate during the strand exchange reaction and ligation reaction.

The stem-and-loop structure (13) in the hairpin-shaped DNA probe (11) contributes to stabilize the single stranded probe itself and to bring the 3' terminus close to the 5' terminus of the hybridized strand of the target DNA. Preferably, the stem portion in the stem-and-loop structure has 12 to 30 nucleotides, the loop portion has 1 to 10 nucleotides, and the total length is 13 to 40 nucleotides. Said probe is constituted so that it does not create a gap between the nucleotide in the 3' terminus of the stem-and-loop structure and the nucleotide in the 5' terminus of the target double strand DNA that has been hybridized to said probe. Preferably, the stem-and-loop structure (13) is long enough to ensure the annealing between self-complementary bases under the hybridization condition for said probe (11) and the target molecule (16).

The method for detecting double stranded DNA employing a hairpin shaped DNA probe In FIG. 1, hairpin shaped DNA probe (11) is contacted with RecA protein (14) to form RecA-probe complex (15). RecA is an enzyme which is involved in homologous recombination in *E. coil.*, and it is activated by binding to a single strand polynucleotides under the existence of ATP. More specifically, RecA has an ATPase activity, and causes the homologous recombination of DNA in such a manner that a double strand DNA is unwound and annealed with another single strand DNA which is partially complementary to the unwound DNA. Thus, when the intermediate complex (15) is contacted with a target DNA (16), RecA unwinds the target double strand DNA and causes strand exchange reaction to form probe-target DNA complex (17). In this strand exchange reaction, if ATP analog such as ATPγS (adenosine 5'-O-(3-thiotriphosphate)) is used instead of ATP, the reaction stops when probe-target DNA intermediate (17) is formed in the strand exchange reaction. In contrast, if ATP is used instead of ATP analogs, the concentration of ADP in the reaction solution increases because of the ATPase activity of the RecA. The increase in ADP concentration causes dissociation of RecA from the recombination intermediate (17), therefore the hybrid nucleic acid will dissociate into the double strand target DNA (16) and the probe (11). By using a ligase on the recombination intermediate, 3' terminus of said probe is ligated to 5' terminus of the target double strand. As is described above, it is not preferred that ATP is used in this reaction system. Therefore, preferred ligase used herein is NAD requiring type. For example, NAD requiring ligase includes a heat-resistance ligase prepared from heat-tolerant bacteria. The ligation temperature is preferably 37 to 65° C. to ensure a stable hybridization and an effective ligation reaction. When the temperature is less than 37° C., the reaction rate of ligation decreases. When the temperature exceeds 65° C., annealing between a probe and a target nucleic acid cannot take place easily. This is because hybrid formation is hindered in both cases. After ligation reaction, deproteinization is performed and then, unhybridized probe is separated from the hybrids. These steps make it possible to clearly detect the target DNA by ligating labeled probe to the terminus of a target DNA.

Modified embodiments

According to the present invention, a hairpin shaped single strand nucleic acid probe molecule for hybridization and the method for detecting a target nucleic acid molecule employing said probe molecule described above include the following modifications.

1) A hairpin-shaped single stranded nucleic acid probe molecule for hybridization which is labeled at other position than 5' end by the strategy well known in the art; and a method for detecting a target nucleic acid molecule employing said probe molecule.

2) A hairpin-shaped single stranded nucleic acid probe molecule having a stem-and-loop structure at 5' side, while in its 3' side, a sequence complementary to the terminal sequence of the target nucleic acid; and a method for detecting a target nucleic acid molecule employing said probe molecule.

3) A method for detecting a single stranded DNA and RNA as a target nucleic acid, comprising a hairpin-shaped single stranded nucleic acid probe molecule for hybridization.

EXAMPLES

Example 1

Figure 2:
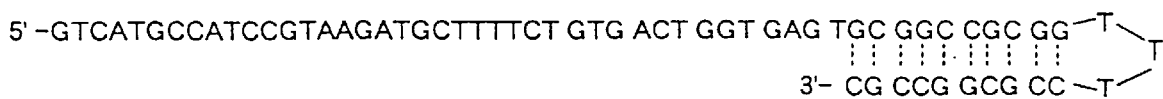
FIG. 2 shows the structure of hairpin-shaped single stranded DNA probe used in the examples of the present invention SEQ ID NO. 1.

Confirmation of sequence specificity during intermediate formation between a hairpin shaped DNA probe and a target DNA Materials and Methods Detection of ScaI-cut linear plasmid DNA, pBluescript SK (–), using a 63 mer hairpin-shaped DNA probe molecule which is labeled with 32P at 5' terminus. The 63 mer hairpin-shaped DNA probe (TRI-20-63) shown in sequence identification No. 1 and FIG. 2 are prepared by the chemical synthesis well known to the skilled in the art and purified by HPLC. Forty nucleotides at the 5' terminus of this probe comprise a sequence which is complementary to the terminal sequence of the ScaI-cut plasmid DNA (pBluescript SK(–)). A commercially available RecA protein was used (Pharmasia Biotech). The following reaction solutions A and B were prepared.

Reaction solution A:

| | |
|---|---|
| 10 × buffer A: | 0.5 micro liter |
| 48 mM ATP γ S: | 0.5 micro liter |
| hairpin shaped probe (TRI-20-63): | 5 ng |
| RecA: | 0.48 micro gram | twice distilled water: up to 5 micro liter

Reaction solution B:

| | |
|---|---|
| 10 × buffer B: | 0.5 micro liter |
| 48 mM ATP γ S: | 0.5 micro liter |
| target linear double stranded DNA: | 100 ng | twice distilled water: up to 5 micro liter.

The 10×buffers and the target linear double stranded DNA are as follows:
10×buffer A:
300 mM Tris-HCl (pH 7.2)/25 mM $(CH_3COO)_2Mg$
10×buffer B:
300 mM Tris-HCl (pH 7.2)/225 mM $(CH_3COO)_2Mg$
Target linear double stranded DNA:
pBluescriptSK(−) (Stratagene) cut with ScaI or EcoRV The above shown reaction solutions A and B was mixed after incubation at 37° C. for 15 min. and then reacted at 37° C. for 30 min. The ligation solution (10 micro liter) of the following composition was added and incubated at 45° C. overnight.

A solution for ligation reaction:

| | |
|---|---|
| • 10 × ampligase DNA ligase RXD buffer: (Epicentre technology) | 2 μL |
| • ampligase: (Epicentre technology) | 20 units (100 units/μL) | twice distilled water up to 10 micro liter

The reaction was stopped by adding 1.8 micro liter of stopping solution (0.22 M EDTA/5.6% SDS). Then, 1 micro liter of proteinase K (10 mg/ml) was added and incubated at 45° C. for 15 min. to decompose proteins. After the reaction, 2 micro liter of BPB dye solution was added and then the sample was electrophoresed through 0.8% agarose gel. The gel was stained with ethidium bromide and photographed and then dried by gel drier. The dried gel was autoradiographed (−80° C., overnight), the X ray film was developed. The electrophoresis pattern in the ethidium bromide-stained gel and that of the autoradiograph were compared.

Results

Figure 3A:
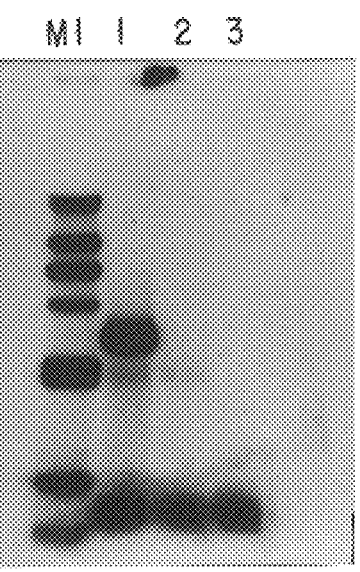
FIG. 3A is an autoradiography, demonstrating the detection of the recombination intermediate formed by the method of the present invention.
Figure 3B:
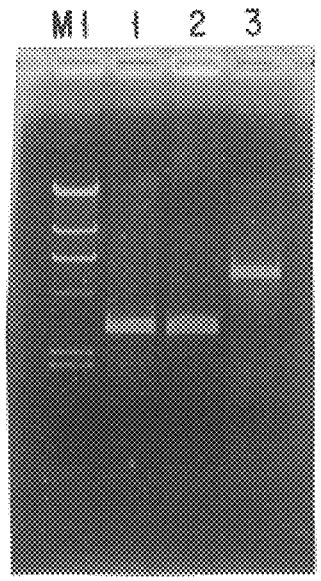
FIG. 3B is a picture of an ethidium bromide-stained gel after electrophoresis, demonstrating the detection of the recombination intermediate formed by the method of the present invention.

FIGS. 3A and 3B summarize the results of the experiments shown above. FIG. 3A shows the result of autoradiography, and FIG. 3B shows ethidium bromide staining pattern of the same gel. In comparing the lane 1 to 3 in the gel of FIG. 3A, the specifically detected band (in lane 1) is the ScaI cut-linear pBluescript SK(−) which was hybridized with the hairpin shaped DNA probe. Although similar amounts of DNA were in both lanes 1 and 2 (see FIG. 3B), the target DNA in lane 2 was not detected because hybridization of a hairpin-shaped DNA probe failed due to the difference in the terminal sequence of the target DNA. FIG. 3B shows that similar amounts of DNA with similar length exist in both lane 1 and lane 2. Lane 3 is a negative control experiment. In this lane, DNA which is not recognized by the probe was used.

Example 2

Confirmation of dependency on RecA and ligase for detection of a double stranded target DNA using hairpin shaped DNA probe Materials and Methods The experimental condition is as shown in Example 1. The reaction conditions for the strand exchange reaction and the following ligation reaction was as follows.

| Combination | RecA | Ligase |
|---|---|---|
| 1 | − | − |
| 2 | + | − |
| 3 | − | + |
| 4 | + | + |

Results

Figure 4A:
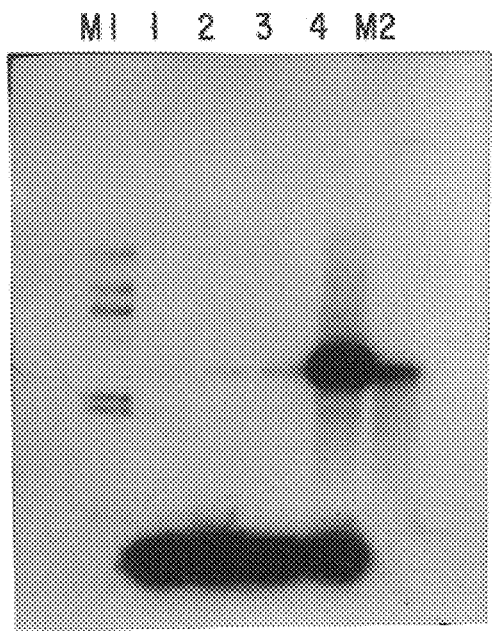
FIG. 4A is an autoradiography, demonstrating RecA and ligase dependent detection of the recombination intermediate formed by the method of the present invention.
Figure 4B:
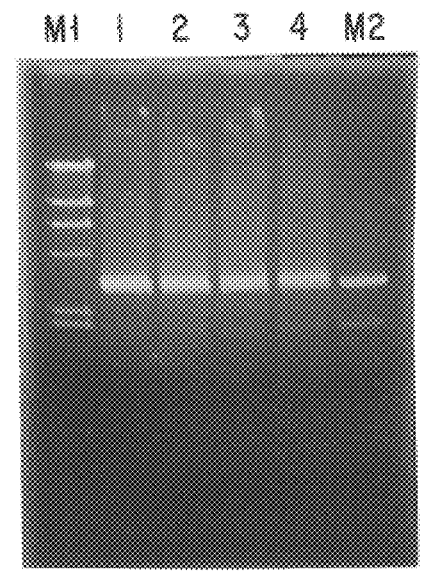
FIG. 4B is a picture of an ethidium bromide-stained gel after electrophoresis, demonstrating RecA dependent detection of the recombination intermediate formed by the method of the present invention.

Results are shown in FIGS. 4A and 4B. FIG. 4A shows autoradiography and FIG. 4B shows ethidium bromide stained gel. Comparison among lanes 1 to 4 shows that the hybrid between a hairpin-shaped probe and the target DNA was detected only in the experiment in which both of RecA and ligase were added. This experiment shows that the hybrid was not formed due to the lack of either RecA or ligase, since under such a condition the hybrid cannot be detected. The gel in FIG. 4B shows all of the lanes contained same amounts of DNA with a same length. When the results in the Example 1 is taken together, it is demonstrated that the combination of RecA and a hairpin-shaped probe having a sequence that is complementary to the terminal sequence of the target nucleic acid molecule ensures the formation and detection of a stable intermediate.

In carrying out the method of the present invention for detecting nucleic acids using the hairpin-shaped single stranded nucleic acid probe for hybridization, there are effects as shown below.

1) Since hybridization between a probe and a target nucleic acid is possible without denaturation of the target nucleic acid, it is possible to detect, in a simple procedure, a long nucleic acid such as a double strand genomic DNA. Therefore, the information of the target nucleic acid itself is obtained.

2) Since the method of the present invention does not require a solid phase support as used in Southern hybridization method, and can be carried out in a test tube, it is possible to handle lots of samples at a time and to obtain, at the same time, a different kind of information of nucleic acid using a different kind of probe.

3) Since all of the components involved in a reaction are in reaction solution, it is possible to increase a reaction rate by increasing a probe concentration.

4) Since all of the reactions are carried out in solution without an aid of a solid phase support, it is possible to lower the background.

5) Since it is not necessary to irradiate a strong ultraviolet light on to the target nucleic acid, the target nucleic acid is not damaged.

Accordingly, the present invention provides a hairpin-shaped nucleic acid probe which enables the formation of a stable hybrid with a target nucleic acid; and a method for detecting nucleic acid having a sequence complementary to the sequence contained in the nucleic acid probe, wherein the hybrid is formed between said hairpin-shaped nucleic acid probe molecule and the target nucleic acid without causing a damage to the target nucleic acid. The present invention is also useful in DNA cloning.

What is claimed is:

1. A method for detecting a target nucleic acid molecule having a certain nucleotide sequence, comprising:

preparing a nucleic acid probe molecule which comprises a first nucleotide portion with self-complementary stem-and-loop; a second nucleotide portion with a single strand structure extending from one end of the first nucleotide portion; and a detectable label bonded to the first or second nucleotide portion, said second nucleotide portion having a sequence complementary to that of at least an end portion of the target nucleic acid molecule to be detected, and said label providing an information that the target nucleic acid molecule is hybridized to the second nucleotide portion;

forming a probe-RecA complex by contacting RecA proteins to the nucleic acid probe molecule;

reacting the probe-RecA complex with a sample containing the double stranded target nucleic acid to form a hybrid in which said second nucleotide portion is hybridized with the end portion of said target nucleic acid molecule;

ligating said first nucleotide portion of the probe molecule to one end of said target nucleic acid molecule in the hybrid by using a ligase;

removing proteins including said RecA from said hybrid;

separating and removing any unhybridized probe molecule from said hybrid; and detecting said label in said hybrid, thereby indicating the presence of said target nucleic acid molecule in said sample.

2. A method according to claim 1, wherein said ligase is an NAD requiring type ligase.

3. A method according to claim 2, wherein the ligase reaction is conducted in a solution at 37 to 65° C.

* * * * *